US009014450B2

(12) United States Patent
Noda

(10) Patent No.: US 9,014,450 B2
(45) Date of Patent: Apr. 21, 2015

(54) METHOD AND APPARATUS FOR FILTERING PROJECTION IMAGES

(71) Applicant: Canon Kabushiki Kaisha, Tokyo (JP)

(72) Inventor: Takeshi Noda, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 74 days.

(21) Appl. No.: 13/706,007

(22) Filed: Dec. 5, 2012

(65) Prior Publication Data

US 2013/0156282 A1 Jun. 20, 2013

(30) Foreign Application Priority Data

Dec. 16, 2011 (JP) ................................. 2011-275380
Oct. 10, 2012 (JP) ................................. 2012-225258

(51) Int. Cl.
*G06K 9/00* (2006.01)
*G06T 11/00* (2006.01)
*G06T 5/20* (2006.01)

(52) U.S. Cl.
CPC ................. *G06T 11/003* (2013.01); *G06T 5/20* (2013.01); *G06T 11/005* (2013.01); *G06T 2207/10112* (2013.01); *G06T 2207/20012* (2013.01); *G06T 2207/20028* (2013.01); *G06T 2211/421* (2013.01)

(58) Field of Classification Search
None
See application file for complete search history.

(56) References Cited

U.S. PATENT DOCUMENTS

| 6,094,467 | A   | * | 7/2000 | Gayer et al. ........................ 378/4 |
| 7,991,243 | B2  |   | 8/2011 | Bal et al. ...................... 382/275 |
| 8,355,594 | B2  |   | 1/2013 | Noda |
| 2005/0213810 | A1 | * | 9/2005 | Sabe et al. .................... 382/159 |
| 2007/0071299 | A1 |   | 3/2007 | Matsuura |
| 2007/0195925 | A1 |   | 8/2007 | Shechter et al. ................ 378/17 |

(Continued)

FOREIGN PATENT DOCUMENTS

| CN | 1939219 A    | 4/2007 |
| JP | H08-019533   | 1/1996 |
| JP | 2006-000226  | 1/2006 |
| JP | 2008-528228  | 7/2008 |

OTHER PUBLICATIONS

A. Manduca et al., "Projection Space Denoising with Bilateral Filtering and CT Noise Modeling for Dose Reduction in CT", *Modern Physics* 36 (11), pp. 4911-4919 (Nov. 2009).

(Continued)

*Primary Examiner* — Atiba O Fitzpatrick
*Assistant Examiner* — Thomas A James
(74) *Attorney, Agent, or Firm* — Fitzpatrick, Cella, Harper & Scinto

(57) ABSTRACT

An image processing apparatus for executing reconstruction of a tomographic image from a plurality of radiation projection images by using a reconstruction filter comprises an obtaining unit that obtains the radiation projection images obtained by detecting X-rays irradiated from a plurality of positions by a digital radiation detector; a reconstructing unit that executes the reconstructing process of the tomographic image on the basis of the obtained radiation projection images and the reconstruction filter; and a processing unit that reduces an influence on a first pixel value of a pixel obtained by the reconstruction filter, that influence having been exerted by a second pixel in which a difference between a pixel value of a target pixel of a filtering process in the radiation projection image and a pixel value of a peripheral pixel of the target pixel is larger than a predetermined threshold value in the reconstructing process.

30 Claims, 12 Drawing Sheets

(56) References Cited

U.S. PATENT DOCUMENTS

| | | | |
|---|---|---|---|
| 2007/0217566 A1* | 9/2007 | Chen et al. | 378/4 |
| 2008/0095437 A1* | 4/2008 | Grindstaff et al. | 382/173 |
| 2008/0267477 A1* | 10/2008 | Conti et al. | 382/131 |
| 2009/0175562 A1* | 7/2009 | Pan et al. | 382/312 |
| 2009/0279768 A1* | 11/2009 | Nishikawa | 382/132 |
| 2011/0158550 A1* | 6/2011 | Noda | 382/264 |
| 2011/0170757 A1* | 7/2011 | Pan et al. | 382/131 |
| 2012/0128225 A1 | 5/2012 | Noda | |
| 2012/0237115 A1* | 9/2012 | Rohkohl et al. | 382/154 |
| 2012/0275656 A1* | 11/2012 | Boese et al. | 382/107 |
| 2013/0070991 A1* | 3/2013 | Yang et al. | 382/131 |
| 2013/0094747 A1* | 4/2013 | Souza et al. | 382/132 |
| 2013/0267841 A1* | 10/2013 | Vija | 600/427 |
| 2014/0010431 A1* | 1/2014 | Stayman et al. | 382/131 |

OTHER PUBLICATIONS

H. Watabe et al., "Nonlinear Filters for Multimedia Applications", IEEE (1999).
O. Demirkaya, "Reduction of Noise and image Artifacts in Computed Tomography by Nonlinear Filtration of the Projection Images", Proceedings of the SPIE 4322, pp. 917-923 (2001).
Extended European Search Report, issued Apr. 8, 2013, in EPO counterpart application 12197177.4-1906.
Chinese Office Action issued in counterpart application No. 201210548846.X dated Aug. 18, 2014, along with its English-language translation (24 pages).
Korean Office Action issued in corresponding application No. 10-2012-0146454 dated Jan. 13, 2015, along with its English-language translation (9 pages).

* cited by examiner

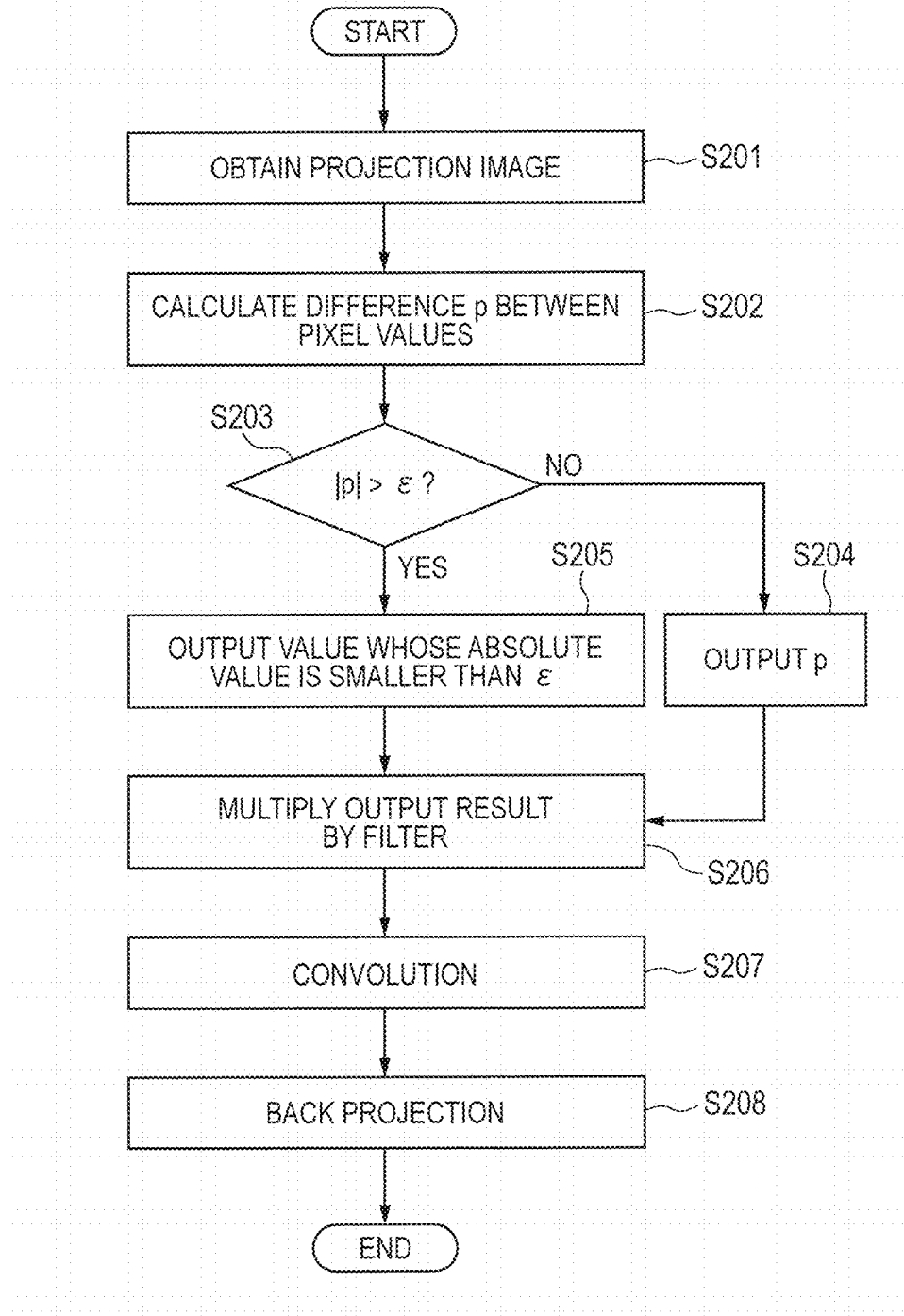

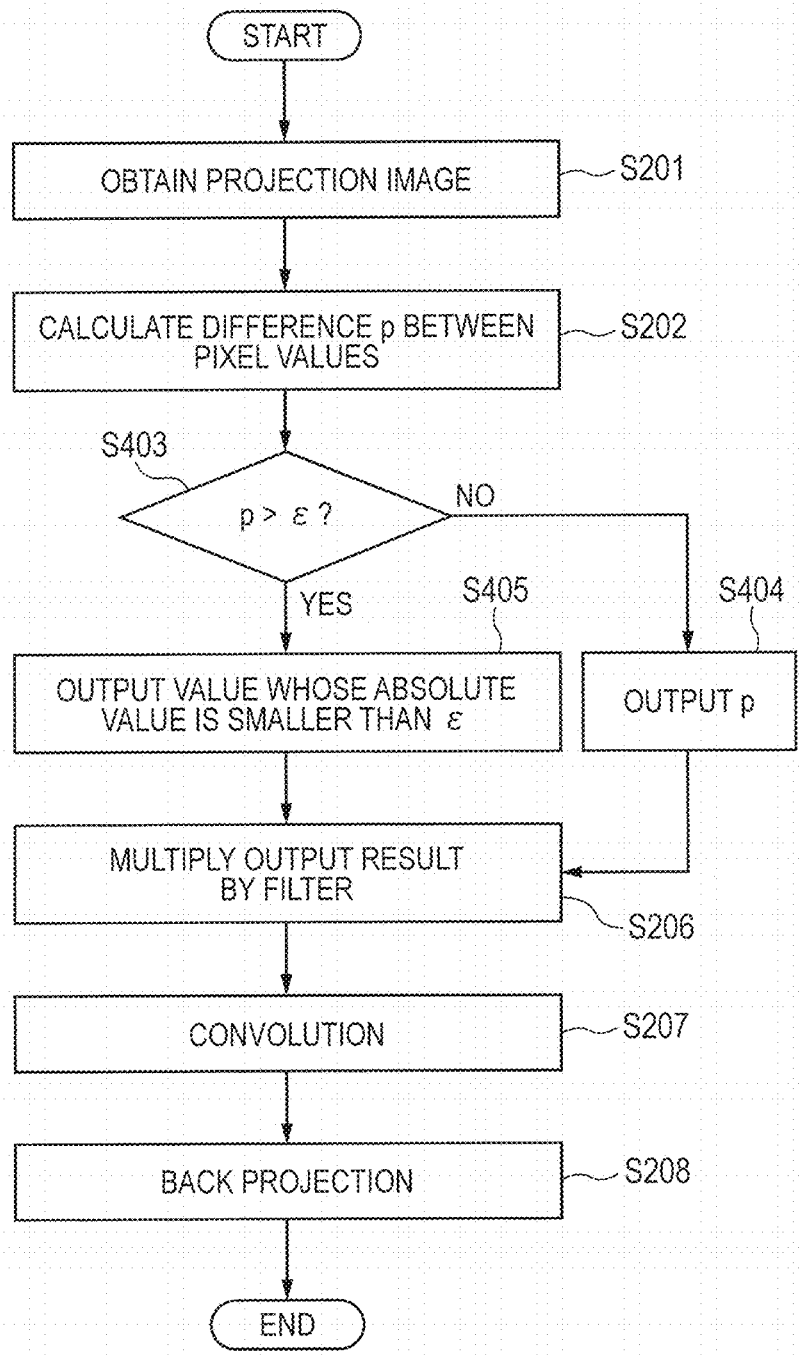

METHOD AND APPARATUS FOR FILTERING PROJECTION IMAGES

BACKGROUND OF THE INVENTION

1. Field of the Invention

The present invention relates to an image processing apparatus, an image processing method, and a program for use in tomographic image interpretation using X-rays.

2. Description of the Related Art

Although 40 years or more have passed since a diagnostic apparatus that creates a tomographic image using an X-ray was developed in the 1970s, it is still developed and active as a diagnostic technique today. In recent years, tomosynthesis for reconstructing a tomographic image by using projection images obtained using a limited angle has also been performed. Although usually used for mammography, such a method may also be used in the investigation of an implant in an orthopaedic image because tomosynthesis enables the obtaining of a tomographic image without needing a large apparatus such as a gantry or the like and a metal artefact is usually small.

Among various methods of reconstructing a tomographic image from projection images, filtered back projection has been used as a method of mathematically obtaining a tomographic image at high speed and with high precision, and this method is a central reconstructing method even now. According to this method, the projection images are filtered using a reconstruction filter such as ramp filter, Shepp & Logan filter, or the like for amplifying a high frequency and, thereafter, back projection is performed. However, if a substance which largely absorbs X-rays such as a piece of metal exists in the human body, there is a problem in that an overshoot or undershoot occurs in a boundary area between the human body and the high absorber and a streak artefact occurs in the tomographic image. Although the reconstruction by the filtered back projection has also been performed even in tomosynthesis in recent years, a streak artefact by the metal still appears as an adverse reaction.

When the streak artefact occurs, a streaky or linear noise around a specific area of an image occurs, so that the representation of a lesion, organs, or the like on the tomographic image is deteriorated and investigative performance of the tomographic image is remarkably deteriorated. To prevent such deterioration, various reducing methods of the streak artefact which occurs by the high absorber have been considered for a long time.

Japanese Patent Application Laid-Open No. H08-019533 discloses a method whereby a high absorber is computationally removed from a projection image, the removed portion is interpolated, and thereafter, a tomogram is reconstructed. Japanese Patent Application Laid-Open No. 2008-528228 discloses a method whereby a direction-dependent adaptive filtering process is performed to a streak artefact in a tomographic image, thereby reducing the streak artefact. Japanese Patent Application Laid-Open No. 2006-000226 discloses a method whereby a reconstruction filter in which a high frequency is suppressed is used in a high absorber and an ordinary reconstruction filter is used in a low absorber, thereby reducing a streak artefact.

According to the method of Japanese Patent Application Laid-Open No. H08-019533 (mentioned above), since the high absorber is interpolated in another portion, there is a possibility that an unnatural tomographic image is produced. On the other hand, in the orthopaedic field or the like, there is a case where the user wants to confirm a state of an embedded implant or metal plate. In such a case, if the high absorber image information is removed, there is a risk that it becomes difficult to investigate. According to the method of Japanese Patent Application Laid-Open No. 2008-528228, since the filtering process is performed to the tomographic image, there is a case where an image blur occurs or there is a possibility that the suppression of the artefact becomes insufficient. According to the method of Japanese Patent Application Laid-Open No. 2006-000226, if the suppression of the high frequency is insufficient, there is a possibility that the suppression of the artefact becomes insufficient, and on the contrary, if the high frequency is excessively suppressed, there is a possibility that an image blur occurs in a low absorber portion such as an organ or the like.

SUMMARY OF THE INVENTION

The invention is made in consideration of the foregoing problems and it is desirable to provide a method whereby when a tomographic image is reconstructed by a filtered back projection, a streak artefact by a high absorber is reduced effectively without causing an image blur.

In order to solve the above problems, the present invention provides an image processing apparatus comprising: an obtaining unit that obtains a plurality of radiation projection images from a digital radiation detector; a reconstructing unit that executes a filtering process on the plurality of radiation projection images using a reconstruction filter and a reconstructing process to create a tomographic image on the basis of the obtained plurality of radiation projection images; and a processing unit that reduces an influence on a value of a first pixel in a radiation projection image to be supplied to the reconstruction unit, the influence being exerted by a second pixel (q'), in a case in which a difference between the value of the first pixel and the value of the second pixel is larger than a predetermined threshold value ($\epsilon$).

According to the invention, in the image reconstruction using the filtered back projection, the streak artefact by the high absorber such as a metal or the like can be reduced effectively without causing the image blur.

Further features of the present invention will become apparent from the following description of exemplary embodiments with reference to the attached drawings.

BRIEF DESCRIPTION OF THE DRAWINGS

FIG. 2 is a flowchart illustrating a flow for an image process in the first embodiment.

FIG. 5 is a flowchart illustrating a flow for an image process in a third embodiment.

DESCRIPTION OF THE EMBODIMENTS

An image processing apparatus, an image processing method, and a program according to an embodiment of the invention will be described in detail hereinbelow with reference to the drawings. Although tomosynthesis will be described as an example hereinbelow, the invention can be also applied to ordinary X-ray computed tomography (CT). The invention can be also applied to a reconstruction using a filtered back projection such as single photon emission computed tomography (SPECT), positron emission tomography (PET), magnetic resonance imaging (MRI), or the like.

<Embodiment 1>

Figure 1:
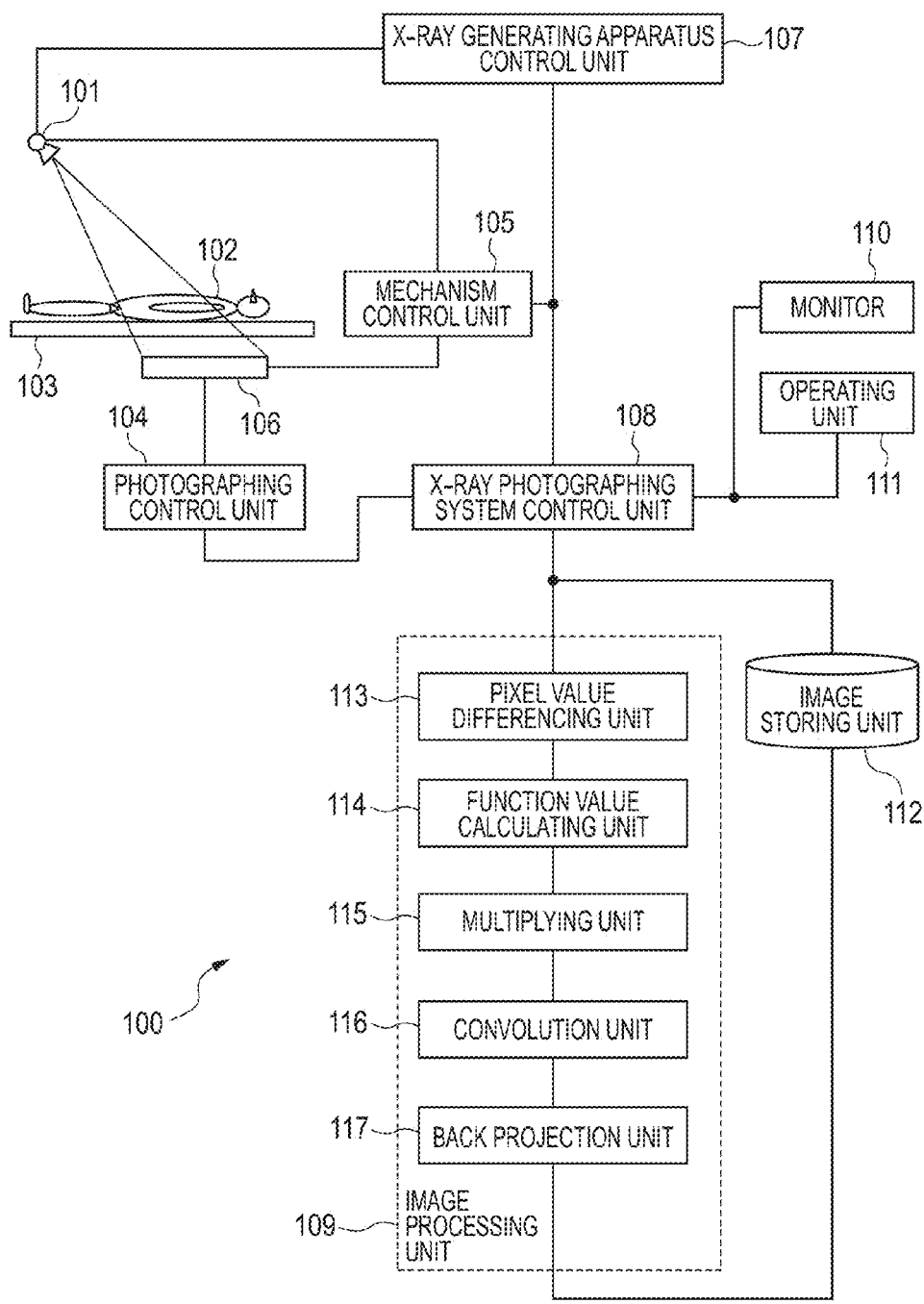
FIG. 1 is a diagram illustrating a functional construction of an image processing apparatus in a first embodiment.

FIG. 1 illustrates a functional construction of an image processing apparatus 100 according to an embodiment 1. An X-ray tube 101 irradiates X-rays from a plurality of irradiation angles. A subject to be tested (hereinbelow, referred to as a subject) 102 is positioned on a bed 103. An X-ray detector 106 receives the X-rays and obtains X-ray images. A mechanism control unit 105 controls positions of the X-ray tube 101 and the X-ray detector 106. A photographing control unit 104 electrically controls the X-ray detector 106 and obtains X-ray images. An X-ray generating apparatus control unit 107 electrically controls the X-ray tube so as to generate the X-rays under predetermined conditions. An X-ray photographing system control unit 108 controls the mechanism control unit 105 and the photographing control unit 104 and in conjunction with the detector 106 obtains X-ray images from a plurality of X-ray irradiation angles.

An image processing unit 109 and an image storing unit 112 are provided for the X-ray photographing system control unit 108 and one or a plurality of computers are built therein. For example, a main control unit such as a CPU (central processing unit) or the like and storing units such as ROM (Read Only Memory), RAM (Random Access Memory), and the like are provided for the computer. A graphic control unit such as a GPU (Graphics Processing Unit) or the like, a communicating unit such as a network card or the like, an input/output unit such as keyboard, display, touch panel, or the like, and so on may be also provided for the computer. Those component units are connected by a bus or the like and are controlled by a method whereby the main control unit executes programs stored in the storing unit. Further, a monitor 110 for displaying photographed projection images and an operating unit 111 which is operated by the user are provided for the output and input of the X-ray photographing system control unit 108.

In accordance with instructions from the X-ray photographing system control unit 108, the image processing unit 109 reconstructs the obtained X-ray images and forms a tomographic image. For this purpose, the image processing unit 109 has a pixel value differencing unit 113, a function value calculating unit 114, a multiplying unit 115, a convolution unit 116, and a back projection unit 117.

A plurality of X-ray images (hereinbelow, also referred to as projection images or radiation projection images) from the various X-ray irradiation angles obtained from the X-ray detector 106 by the X-ray photographing system control unit 108 through the photographing control unit 104 are input to the image processing unit 109. A defect correction, a gain correction, a logarithmic transformation, and the like are preliminarily performed to the projection images.

The pixel value differencing unit 113 calculates a difference value between the value of a filtering target pixel and the value of a pixel which exists around the filtering target pixel (i.e. a peripheral pixel or a neighbouring pixel) and which is used for a filtering process.

On the basis of the difference value calculated in the pixel value differencing unit 113, when an absolute value of the difference value is equal to or smaller than a predetermined value, the function value calculating unit 114 outputs the difference value as it is, and when the absolute value is larger than the predetermined value, the function value calculating unit 114 outputs a value having an absolute value that is smaller than the absolute value of the difference value and having a sign that is the same as that of the difference value. This output value may be, for example, equal to 0.

The multiplying unit 115 multiplies an output of the function value calculating unit 114 by a reconstruction filter coefficient. As a reconstruction filter, an ordinary filter which is used in a filtered back projection such as ramp filter, Shepp & Logan filter, or the like is used. The convolution unit 116 executes a filtering process to the projection images by using the reconstruction filter coefficient used in the multiplying unit 115.

The back projection unit 117 executes a back projection by using the filtered projection images and forms a tomographic image. The back projection includes a step of performing an integrating process to the reconstruction-filtered projection images. In the case of reconstruction using a superimposed integrating method in a real space, theoretically, the reconstruction-filtered projection images are integrated with respect to an irradiation angle θ. For the integration, the irradiation angle is, for example, an angle between 1) the direction connecting a centre of a radiation detector and a focal point of the X-ray tube, and 2) the direction perpendicular to the detecting surface of the radiation detector. Since the radiation projection images which are actually obtained are discrete, an approximate integrating process is executed in consideration of such a focal point. Thus, the tomographic image can be formed in which a streak artefact due to the high absorber is eliminated and the image blur hardly occurs. A frequency response of the filter does not change throughout this integrating process.

An example of an image processing flow in the image processing apparatus 100 illustrated in FIG. 1 will be described with reference to FIG. 2.

First, projection images are obtained in S201. They are obtained by photographing the subject 102 using X-rays while changing the X-ray irradiation angle of the X-ray tube 101 within a range from −40° to 40°. Any number of photograph images can be obtained. For example, if 80 projection images are photographed at 15 FPS (frames per second) while changing the angle one degree (1°) at a time, the images can be collected in about 6 seconds. Any photographing condition of the X-ray can furthermore be set, but it is sufficient to photograph the images at about 100 kV and 1 mAs in the case of photographing a human chest or the like. A distance between the X-ray detector 106 and the X-ray tube 101 is set to a setting range of about 100 to 150 cm.

The X-ray detector 106 is moved parallel, but in the direction opposite, to the X-ray tube 101. A parallel movement amount at this time is obtained by Ptanβ assuming that a projection angle is set to β and a distance between a rotational centre of the X-ray tube 101 and a centre of the X-ray detector 106 is set to D. If the X-ray detector 106 is moved parallel to the X-ray tube as mentioned above, even if the X-ray irradiating direction of the X-ray tube 101 is changed, a reference axis always passes through the centre of the X-ray detector 106.

The obtained series of projection images are subjected to pre-processes and, thereafter, the projection images are input to the image processing unit 109. Pre-processes may include a correction of defective pixels and a dark current of the X-ray detector 106, a correction of an irradiation fluctuation that is caused by the X-ray tube 101, a logarithmic transformation, and the like. It is sufficient to use the processes as these pre-processes which are generally executed in the X-ray detector. For the logarithmic transformation, the pixel values of the projection images are set to values obtained by linearly integrating an X-ray attenuation coefficient. The X-ray images are reconstructed on the basis of the additivity of the X-ray attenuation coefficient.

In S202, a difference value p between a filtering target pixel and a peripheral pixel which is used in the filtering process is calculated by using the pixel value differencing unit 113. The difference may be, for instance, in intensity, luminance or shade in a greyscale.

Figure 3A:
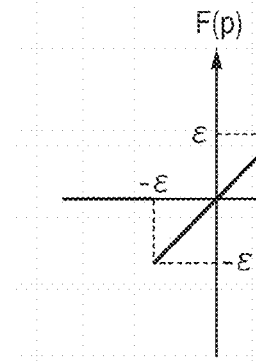
FIGS. 3A, 3B and 3C are diagrams each illustrating an example of an output of a function in the first embodiment.
Figure 3B:
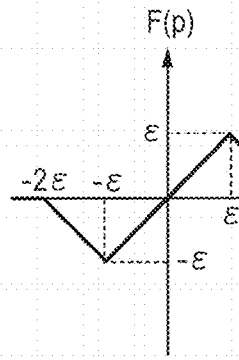
Figure 3C:
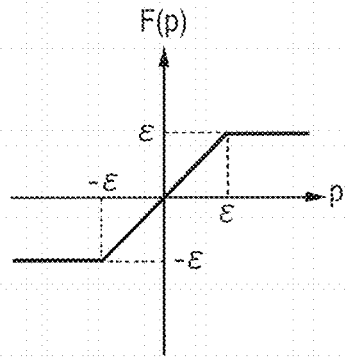

In S203, an absolute value |p| of the difference value calculated in S202 is compared with a predetermined threshold value ε. Thus, if the absolute value |p| is equal to or smaller than the threshold value ε, the difference value p is output in S204. If the absolute value |p| is larger than the threshold value ε, a value with an absolute value equal to or smaller than the threshold value ε, for example, 0, ±ε, ±(2ε−|p|), or the like is output in S205. The processes of S203 to S205 are executed by the function value calculating unit 114 and their results are expressed by a piecewise linear function F(p) as shown in FIGS. 3A to 3C. In the piecewise linear function F(p) shown in FIGS. 3A to 3C according to the embodiment, the difference value (if p has a value up to ε) or the value smaller than the difference value is output on the basis of a magnitude relation between the threshold value and the difference value between the pixel value of the processing target pixel by the reconstruction filter and the pixel value of the peripheral pixel (of the target pixel of the filtering process) which is used in the reconstruction filtering process. The effect in the image is a reduced contrast between neighbouring pixels in the case where the input contrast is very high (over the threshold). Such characteristics contribute to the proper reduction of the metal artefact, which appears as a high contrast artefact.

In S206, a reconstruction filter function such as ramp filter, Shepp & Logan filter, or the like is multiplied by an output result, that is, F(p) in S204 and S205, using the multiplying unit 115. That is, the reconstruction filter function is converted into what is called an epsilon (ε) filter function using an epsilon (ε) filter. According to the characteristics of the ε filter, the difference value (hereinbelow referred to as a difference signal) between the target pixel (targeted for processing) and the peripheral pixel is used as local information, and when the difference signal is small, it is considered that a correlation between the processing target pixel and the peripheral pixel is strong, and it is intended to actively use that peripheral pixel. By this method, an influence of the pixel value which differs significantly (i.e. which has a high contrast) from an object portion such as a metal or the like can be reduced. In the ε filter, since the difference between the pixel values is used as a threshold value ε, that is, a parameter, the parameter can be more properly and easily adjusted with respect to the projection images which are obtained by the radiography. In another embodiment, a data-dependent type of process serving as a process for changing the coefficient of the filter in accordance with a nature of the image can be also used in place of the ε filter.

In S207, a reconstruction filter h(t) multiplied by F(p) in S206 is convoluted to the projection images. This process is executed in the convolution unit 116 and is expressed by the following equation (1) in the case of the tomosynthesis.

$$G(x_t', z_t, \beta) = \int_{-\infty}^{\infty} F(q(x_t, z_t, \beta) - q(x_t', z_t, \beta)) h(x_t' - x_t) J_C(x_t, z_t, \beta) dx_t \quad (1)$$

Where $x_t$ and $z_t$ denote coordinates on the X-ray detector 106. $x_t$ indicates the coordinate which is parallel with the moving direction of the X-ray detector 106. $z_t$ indicates the coordinate which is perpendicular to the moving direction of the X-ray detector 106. β denotes the projection angle. $q(x_t, z_t, \beta)$ denotes pixel values on the X-ray detector 106. $J_c$ denotes a coefficient for converting an integration variable into a geometrical construction of the tomosynthesis. $J_c$ is expressed by the following equation (1-1).

$$J_C(x_t, z_t, \beta) = \frac{D_t + x_t \sin\beta_t}{\sqrt{D_t^2 + 2x_t D_t \sin\beta_t + x_t^2}} \quad (1-1)$$

$$D_t = \sqrt{D^2 + z_t^2}$$

$$\sin\beta_t = \frac{D\sin\beta}{\sqrt{D^2 + z_t^2}}$$

Figure 12:
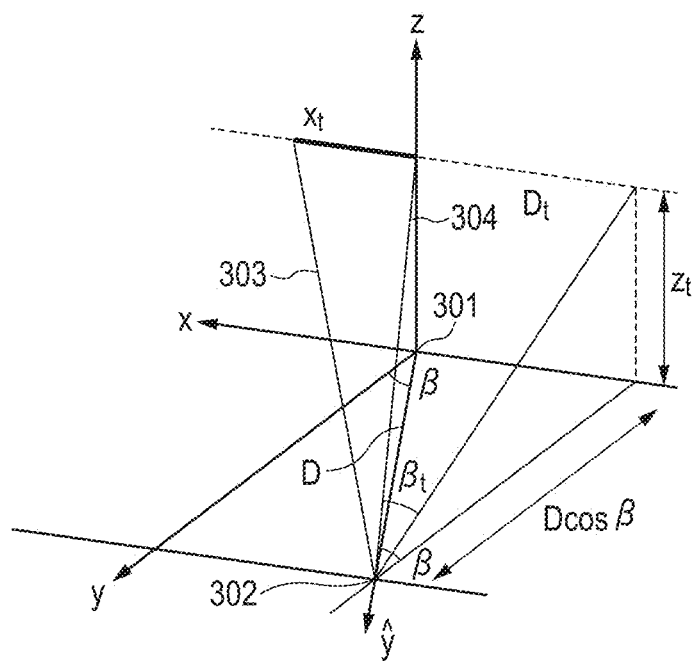
FIG. 12 is a diagram illustrating relations among variables of 3-dimensional coordinate axes in the first embodiment.

Relations among the variables in the equation (1-1) are illustrated in FIG. 12. 3-dimensional coordinate axes x, y, and z denote a reconstruction coordinate space and an isocenter is used as an origin. An xz plane is a plane which is parallel with a detecting surface of the X-ray detector 106 and is a plane which passes through an isocenter 301. The y axis is a normal which is perpendicular to the detecting surface of the X-ray detector 106. $x_t$ and $z_t$ denote the x coordinate and the z coordinate of a point at which a straight line 303 connecting a point on the X-ray detector 106 and a focal point 302 of the X-ray tube 101 crosses the xz plane. The angle β between the y axis and a reference axis of the X-ray tube 101 is an X-ray irradiation angle (projection angle). The equation (1-1) expresses a cosine value of an angle between the straight lines 303 and 304. The straight line 304 is a line connecting the focal point 302 and a point at which a perpendicular put down to the z axis from a point where the straight line 303 crosses the xz plane. The value for line 303 is $\sqrt{(x_t + \sin\beta_t)^2 + (D_t \cos\beta_t)^2}$ and the value for line 304 is $D_t$ so that the cosine of the angle between lines 303 and 304 can be determined using the cosine rule, giving $J_c$.

By applying the convolution of equation (1) to $J_c$, a 2-dimensional filtered projection image $G(x_t', z_t, \beta)$ is obtained where $x_t'$ is a pixel position (or, more specifically, a distance from the z-axis) of a neighbouring or peripheral pixel.

Since the actual calculations are discretely performed by using a computer, a calculating method at the time when the above equations are applied to a discrete system will now be clarified.

Figure 13:
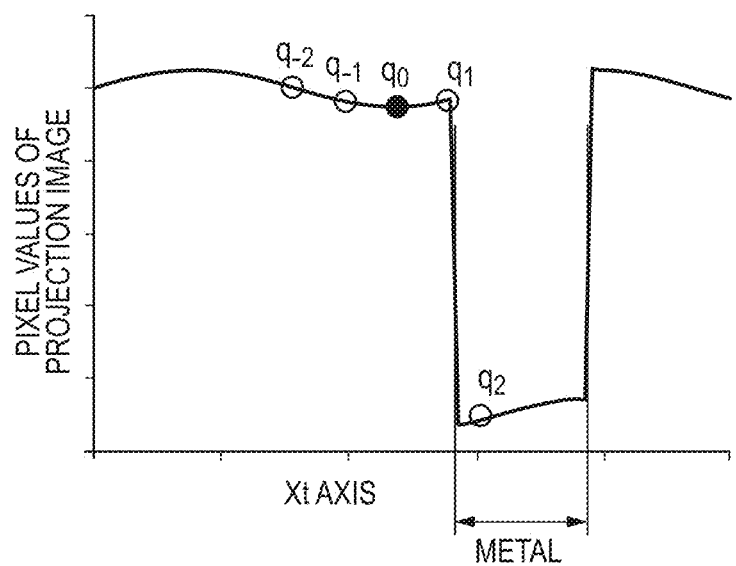
FIG. 13 is a diagram illustrating a change in pixel value of a projection image in the first embodiment.

For convenience of explanation, a consideration will be made with respect to only the $x_t$ axis and $J_c$ which expresses the tomosynthesis geometrical construction is omitted. In the discrete system, an adding process is executed as an integration. As illustrated in FIG. 13, as compared with the ordinary object portion, since the metal portion extremely strongly absorbs the X-ray, the pixel values decrease suddenly. In the reconstruction filtering process, it is assumed that a target pixel is set to •, peripheral pixels are set to ○, each pixel value is set to $q_N$, and a filter coefficient is set to $h_N$.

At this time, the filtering process according to the method in the related art is expressed by the following equation (1-2).

$$G_0 = h_{-2}q_{-2} + h_{-1}q_{-1} + h_0 q_0 + h_1 q_1 + h_2 q_2 \qquad (1\text{-}2)$$

The filtering process according to the invention is expressed by the following equation (1-3).

$$G_0 = h_{-2}F(q_{-2}-q_0) + h_{-1}F(q_{-1}-q_0) + h_0 F(q_0-q_0) + h_1 F(q_1-q_0) + h_2 F(q_2-q_0) \qquad (1\text{-}3)$$

When F denotes the piecewise linear function as shown in FIG. 3A and a difference between $q_0$ and each $q_N$ lies within ε, the equation (1-3) is expressed by the following equation (1-4).

$$G_0 = h_{-2}q_{-2} + h_{-1}q_{-1} + h_0 q_0 + h_1 q_1 + h_2 q_2 - (h_{-2} + h_{-1} + h_0 + h_1 + h_2)q_0 \qquad (1\text{-}4)$$

Since a DC component of the reconstruction filter is equal to 0, a value in brackets ( ) in the equation (1-4) is equal to 0, so that the equation (1-4) is equal to the equation (1-2). When the metal exists in the image as illustrated in FIG. 13 and a difference between $q_2$ and $q_0$ exceeds ε, the equation (1-3) is expressed by the following equations (1-5).

$$\begin{aligned} G_0 &= h_{-2}q_{-2} + h_{-1}q_{-1} + h_0 q_0 + h_1 q_1 - \\ &\quad (h_{-2} + h_{-1} + h_0 + h_1)q_0 \\ &= h_{-2}q_{-2} + h_{-1}q_{-1} + h_0 q_0 + h_1 q_1 + \\ &\quad h_2 q_0 (h_{-2} + h_{-1} + h_0 + h_1 + h_2)q_0 \\ &= h_{-2}q_{-2} + h_{-1}q_{-1} + h_0 q_0 + h_1 q_1 + h_2 q_0 \end{aligned} \qquad (1\text{-}5)$$

That is, $q_2$ is eliminated from the filtering process and, in place of it, $h_2$ is multiplied by $q_0$. Consequently, in the reconstruction filtering process to the pixel of $q_0$, a process for reducing an influence of the pixel of $q_2$ which is exercised on a pixel $G_0$ that is obtained after the process can be performed. That is, when $G_0$ is obtained, for example, the influence of the pixel of $q_2$ whose pixel value differs significantly from that of the pixel of $q_0$ is weakened by the influence of the metal and such an effect that the pixel value is corrected so as not to be largely changed is obtained. Thus, the influence of the metal to cause the sudden change in pixel value is suppressed and the occurrence of the streak artefact in the tomographic image can be prevented. Since use of a low pass filter or the like as in the method in the related art is unnecessary, an adverse reaction such as an image blur or the like is also reduced or eliminated.

In another embodiment, since it is sufficient that a value corresponding to the equations (1-5) is obtained, it is desirable that a process for changing $h_2 q_2$ in the equation (1-2) to $h_2 q_0$ or the like in the equations (1-5) is executed. That is, so long as the process for reducing the influence of $q_2$ is executed, various changes are possible. For example, in order to obtain a value corresponding to $h_2 q_0$ mentioned above, by changing the coefficient of the reconstruction filter in such a manner that $h_2$ is changed to $h_2'$ or the like without changing $q_2$ to $q_0$, the influence which is exerted on $G_0$ by $q_2$ can be equivalently reduced. On the other hand, for example, a process for correcting the obtained $G_0$ and reducing the influence of $q_2$ may be executed.

In the example of the process applied to the pixel of $q_0$ mentioned above, the nonlinear function shown in FIG. 3A is used as an example. However, the invention is not limited to it but even if a function shown in FIG. 3B or FIG. 3C is used, such a reconstruction can be performed that the influence of the pixel of the metal portion is reduced.

Returning to FIG. 2, in S208, by back projecting the 2-dimensional filtered projection image $G(x_t', z_t, \beta)$, a tomographic image $f(\vec{r})$ in arbitrary 3-dimensional coordinates $\vec{r}$ is formed. This process is executed in the back projection unit 117 and is expressed by the following equation (2).

$$f(\vec{r}) = \int_{-\beta_m}^{\beta_m} d\beta J_B(x_t', z_t, \beta, \vec{r}) G(x_t', z_t, \beta) \qquad (2)$$

In the equation (2), $\beta_m$ denotes a maximum projection angle. $J_B$ denotes a coefficient for converting an integration variable into a geometrical construction of the tomosynthesis and is expressed by the following equation (2-1).

$$J_B(x_t', z_t, \beta, \vec{r}) = \frac{D\cos\beta}{\sqrt{D^2\cos^2\beta + z_t^2}} \frac{(D_t + x_t'\sin\beta_t)^2}{\cos\beta_t \left(D_t - \frac{D_t}{D}\vec{r}\cdot\hat{y}\right)^2} \qquad (2\text{-}1)$$

Where, $\vec{r}$ denotes a 3-dimensional vector showing a reconstruction point in which the isocentre is set to an origin. $\hat{y}$ denotes a unit vector along the reference axis (centre of the beam) of the X-ray tube. Thus, the tomographic image $f(\vec{r})$ can be obtained in which the streak artefact by the high absorber is suppressed. Naturally, the calculations of the above equations are actually executed by a discrete adding process to the data obtained by the discrete system.

Although the embodiment has been described above with respect to the case of the tomosynthesis as an example, the invention can be also applied to the ordinary X-ray CT. The invention can be also applied to the reconstruction using the filtered back projection such as SPECT, PET, MRI, or the like. As a reconstructing method in the case of applying the invention to them, it is sufficient to use a Feldkamp method or a fan beam reconstructing method which is generally used.

<Embodiment 2>

Figure 4:
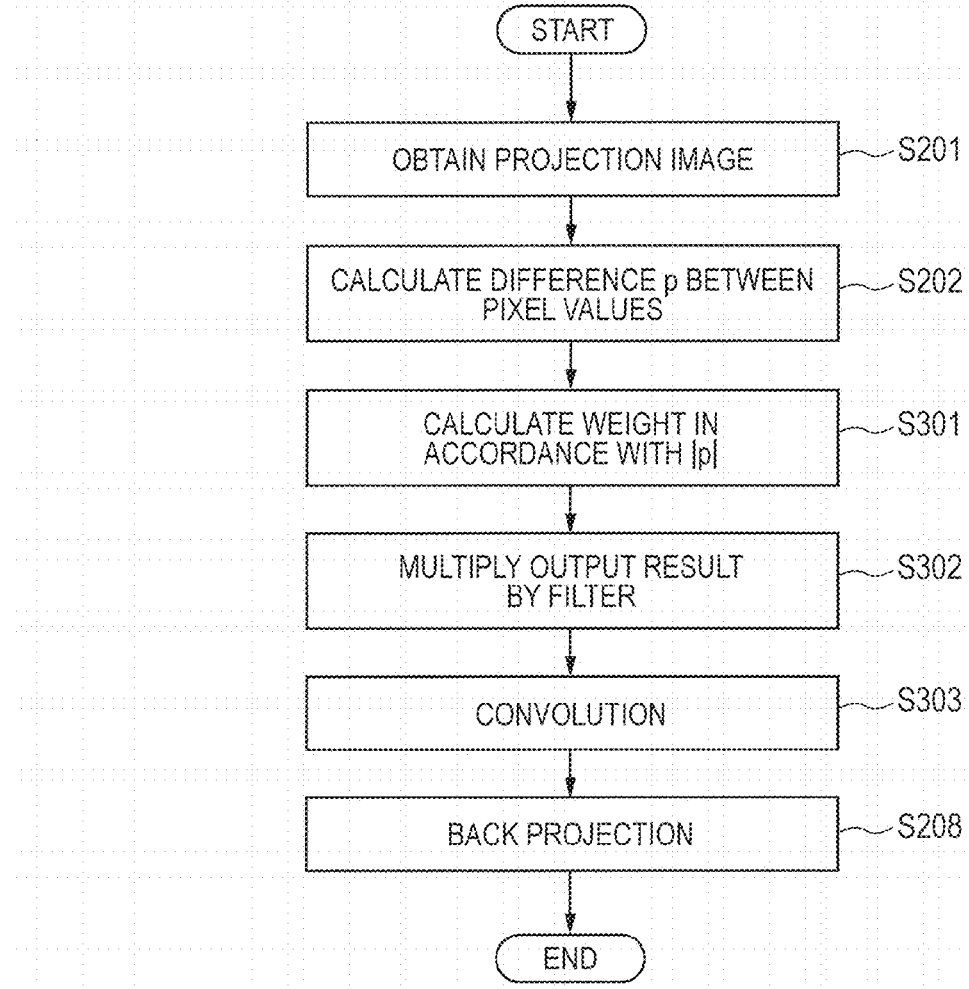
FIG. 4 is a flowchart illustrating a flow for an image process in a second embodiment.

Subsequently, a flow for an image process in an embodiment 2 will be described with reference to FIG. 4. A functional construction is substantially the same as that of the embodiment 1 and is as illustrated in FIG. 1, a processing flow is also substantially the same as that of the embodiment 1, and a description of overlapped portions is omitted here.

The processes of S201 and S202 are the same as those in the embodiment 1. Subsequently, a process of S301 is executed by using the function value calculating unit 114 in place of the processes of S203 to S205 in the embodiment 1. That is, in S301, a weight coefficient is calculated in accordance with the absolute value |p| of the difference value. For example, it is expressed by the following equation (3).

$$w(q(x_t', z_t, \beta) - q(x_t, z_t, \beta)) = \exp\left(-\frac{(q(x_t', z_t, \beta) - q(x_t, z_t, \beta))^2}{2\sigma^2}\right) \qquad (3)$$

Where σ denotes a value which is experimentally decided in accordance with a photographing region or the like and is set in a manner similar to ε in the embodiment 1.

In S302, the reconstruction filter function such as ramp filter, Shepp & Logan filter, or the like is multiplied by a weight output result w(t) of S301 by the multiplying unit 115.

In S303, the reconstruction filter h(t) multiplied by w(t) in S302 undergoes convolution. This process is executed by the convolution unit 116 and is expressed by the following equation (4).

$$G(x_t', z_t, \beta) = \int_{-\infty}^{\infty} w \cdot h(x_t' - x_t) q(x_t, z_t, \beta) J_C(x_t, z_t, \beta) dx_t \quad (4)$$

By the convolution, the 2-dimensional filtered projection image $G(x_t', z_t, \beta)$ is obtained. The process of S208 is the same as that in the embodiment 1.

By the processes of S301 to S303, an influence which is exerted on the reconstruction filtering by the edge of the high absorber such as a metal or the like decreases. Thus, the streak artefact caused by the metal is reduced effectively from the tomographic image. Since the frequency characteristics of the filter are not easily deteriorated, an adverse reaction such as an image blur or the like is also less likely. According to this method, although the DC component of the filter is not stored, if the DC component is adjusted by calculating the DC component by adding the filter coefficient obtained as a result of the process of S302 and by subtracting from the filter coefficient, the DC component can be stored.

<Embodiment 3>

A flow for an image process in an embodiment 3 will be described with reference to FIG. 5. A functional construction is substantially the same as that of the embodiment 1 and is as illustrated in FIG. 1, a processing flow is also substantially the same as that of the embodiment 1, and a description of overlapping portions is omitted here.

Although the streak artefact caused by the high absorber can be reduced effectively by the method and apparatus in embodiment 1, there is a case where a contrast of the high absorber is also deteriorated. In the orthopaedic field or the like, there is a case where the user wants to confirm a state of an embedded implant or metal plate, or the like. In this embodiment, in order to satisfy such a request, the contrast of the high absorber is also maintained and the streak artefact is reduced.

Figure 6A:
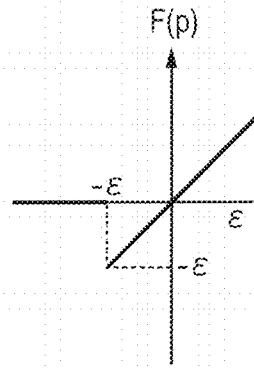
FIGS. 6A, 6B and 6C are diagrams each illustrating an example of an output of a function in the third embodiment.
Figure 6B:
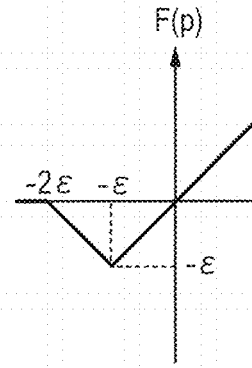
Figure 6C:
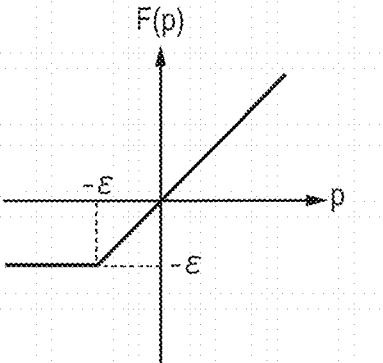

The processes of S201 and S202 are the same as those in the embodiment 1. Subsequently, a process of S403 is executed by using the function value calculating unit 114 in place of the process of S203 in the embodiment 1. That is, in S403, the difference value p calculated in S202 is compared with the predetermined threshold value ϵ. Thus, if the difference value p is equal to or smaller than the threshold value ϵ, the difference value p is output as it is in S404. If the difference value p is larger than the threshold value ϵ, a value with an absolute value smaller than or equal to the threshold value ϵ, for example, 0, ±ϵ, ±(2ϵ−|p|), or the like is output in S405. The processes of S403 to S405 are executed by the function value calculating unit 114 and their results are expressed by the piecewise linear function F(p) as shown in FIGS. 6A to 6C. Processes of S206 to S208 are the same as those in the embodiment 1. If the pixel values of the projection images have been reversed, it is sufficient to exchange the magnitude relations mentioned above. Although the equation to subtract the target pixel of the filtering process from the peripheral pixel has been used in the foregoing processes, on the contrary, if a subtraction is performed, the positive or negative sign of the threshold value is reversed. In the reconstruction filter according to the embodiment of the invention illustrated in FIGS. 6A to 6C, if the absolute value of the difference value between the pixel value of the processing target pixel and the pixel value of the peripheral pixel (of the target pixel of the filtering process) which is used in the reconstruction filtering process is smaller than the threshold value, the difference value is output. If the absolute value of the difference value is larger than the threshold value, a value smaller than the difference value is output. Thus, while the metal portion is extracted to the tomosynthesis image, the metal artefact can be reduced.

By using the piecewise linear function F(p) which is axis-asymmetrical at the origin as shown in FIGS. 6A to 6C, the influence of the high absorber can be eliminated in the filtering of the low absorber portion. Thus, the streak artefact can be suppressed. Since the frequency response of the filter does not change, the image blur is also reduced. On the other hand, the low absorber portion is also considered in the filtering of the high absorber portion. Consequently, the contrast in the high absorber portion can be maintained.

<Embodiment 4>

Figure 7:
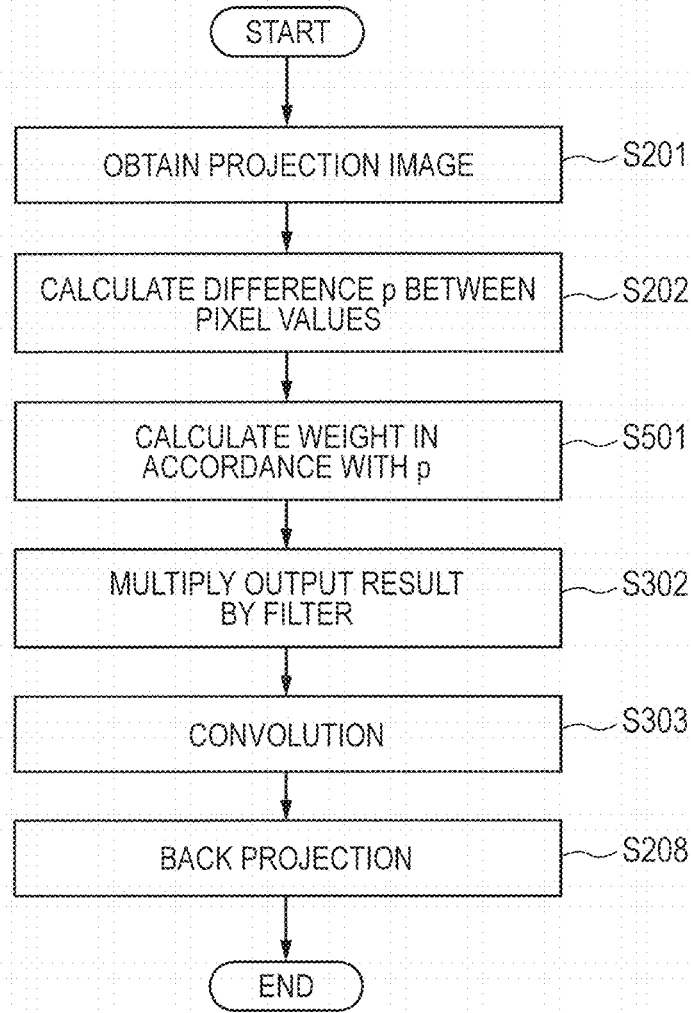
FIG. 7 is a flowchart illustrating a flow for an image process in a fourth embodiment.
Figure 8:
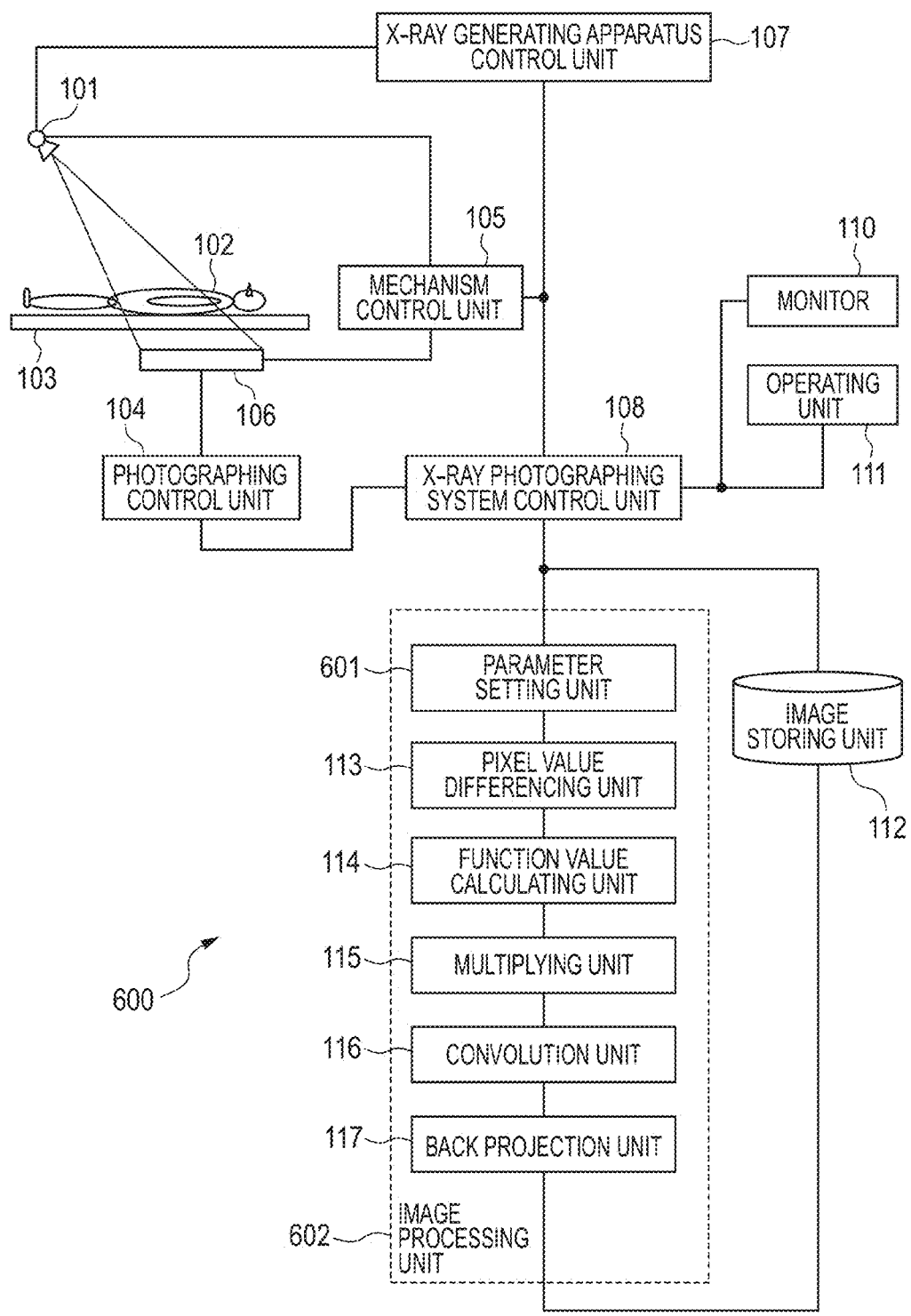
FIG. 8 is a diagram illustrating a functional construction of an image processing apparatus in a fifth embodiment.
Figure 9:
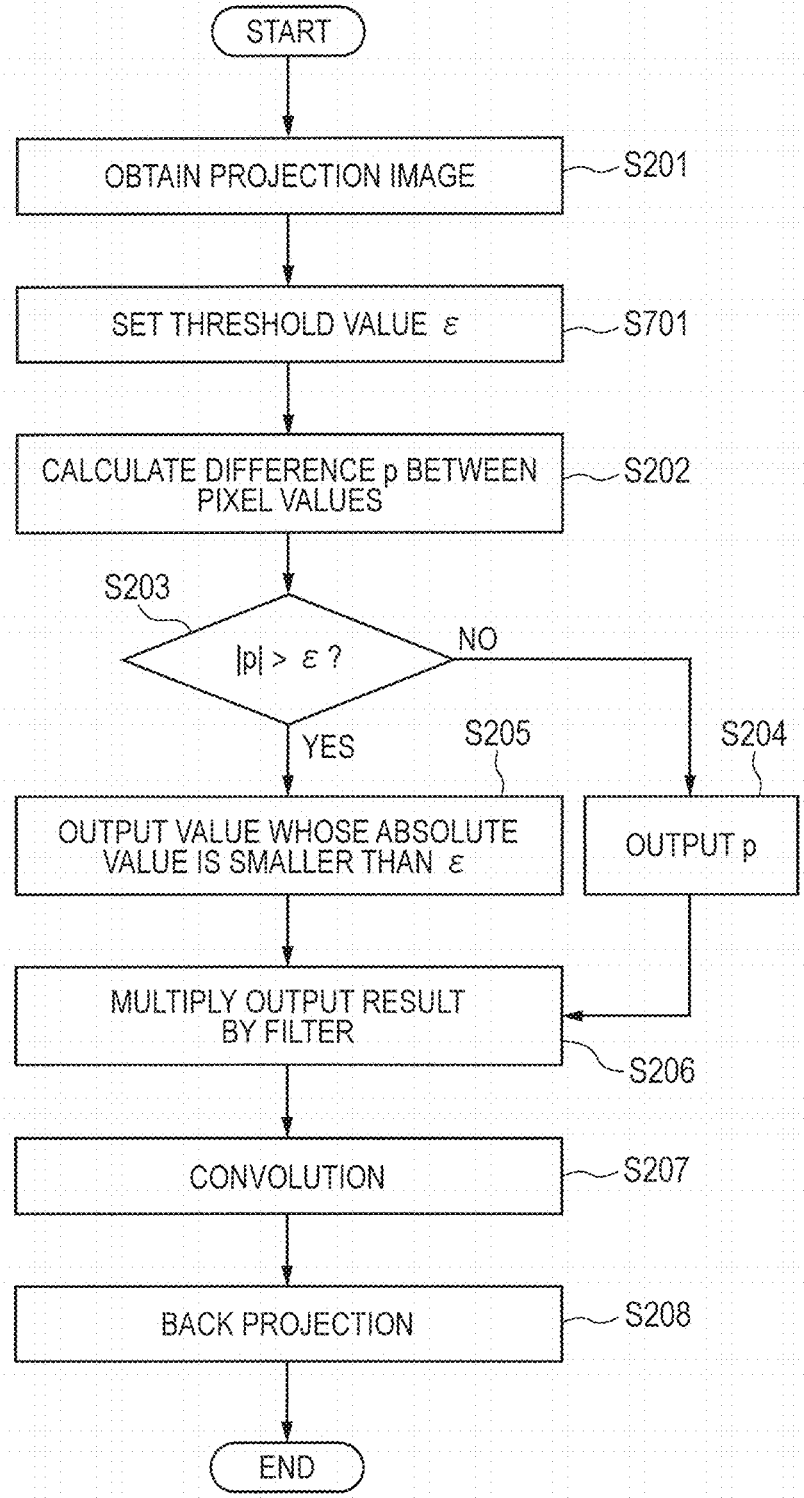
FIG. 9 is a flowchart illustrating a flow for an image process in the fifth embodiment.

Subsequently, a flow for an image process in an embodiment 4 will be described with reference to FIG. 7. A functional construction is substantially the same as that of the embodiment 2 and is as illustrated in FIG. 1, a processing flow is also substantially the same as that of the embodiment 2, and a description of overlapping portions is omitted here.

Although the streak artefact by the high absorber can be effectively reduced by embodiment 2, there is a case where the contrast of the high absorber is also deteriorated. In the orthopaedic field or the like, there is a case where the user wants to confirm a state of an embedded implant or metal plate, or the like. In the embodiment, in order to satisfy such a request, the contrast of the high absorber is also maintained and the streak artefact is reduced.

The processes of S201, S202, S302, S303, and S208 are the same as those in embodiment 2 and only the process of S501 differs. That is, the process of S501 is executed using the function value calculating unit 114 in place of the process of S301 in embodiment 2. In S501, a weight coefficient is calculated in accordance with a difference. This process is expressed by the following equations (5) and (6):

When $q(x_t', z_t, \beta) - q(x_t, z_t, \beta) < 0$, $$w(q(x_t', z_t, \beta) - q(x_t, z_t, \beta)) = \exp\left(-\frac{(q(x_t', z_t, \beta) - q(x_t, z_t, \beta))^2}{2\sigma^2}\right) \quad (5)$$

And when $q(x_t', z_t, \beta) - q(x_t, z_t, \beta) \geq 0$, $$w(q(x_t', z_t, \beta) - q(x_t, z_t, \beta)) = 1 \quad (6)$$

By using the weight which is axis-asymmetrical at the origin as shown in the equation (6), the influence of the high absorber can be reduced in the filtering of the low absorber portion. Thus, the streak artefact can be suppressed. Since the frequency response of the filter is not easily changed, the image blur is also reduced. On the other hand, the low absorber portion is also considered in the filtering of the high absorber portion. Consequently, the contrast in the high absorber portion can be maintained.

<Embodiment 5>

A flow for an image process in an embodiment 5 will be described with reference to FIGS. 8 to 11. An image processing apparatus 600 illustrated in FIG. 8 differs from the image processing apparatus 100 of the embodiment 1 with respect to a point that in an image processing unit 602, a parameter setting unit 601 is added to the image processing unit 109 of the embodiment 1. An image process shown in FIG. 9 differs from the image process in the embodiment 1 with respect to a point that a process of S701 is added to the process shown in FIG. 2. In the embodiment, a specific setting method of the threshold value ϵ will be described in such a form. It can be easily presumed that the setting method of the embodiment can be also applied to the embodiments 2 to 4.

Figure 10:
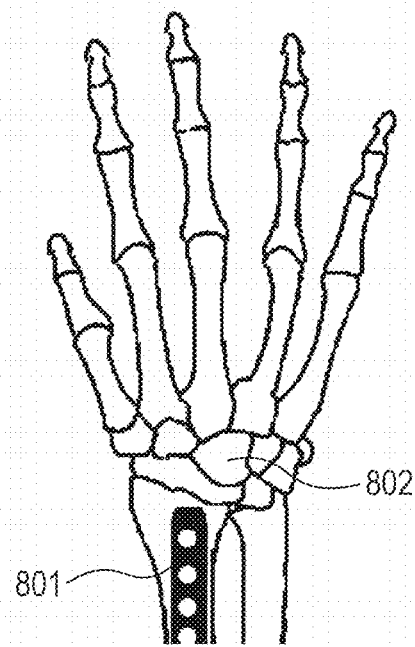
FIG. 10 is a diagram illustrating an example of a setting of a concerned area in the fifth embodiment.

In order to allow the invention to be effectively embodied, it is important that a set value of the threshold value ∈ is proper. In order to set the threshold value ∈, the photographed projection image is displayed to the monitor 110. In the operating unit 111, the user designates two points, one being of a metal portion 801 and another being of a bone portion 802 on the projection image as illustrated in FIG. 10. In S701, a difference between pixel values of those two designated portions is calculated and set to the threshold value ∈ by the parameter setting unit 601.

In the cases of the embodiments 2 and 4, for example, ∈ is regarded as FWHM (full width at half maximum) and it is sufficient to set it as shown by the following equation.

$$\sigma = \epsilon/(2\sqrt{2\ln 2})$$

Figure 11:
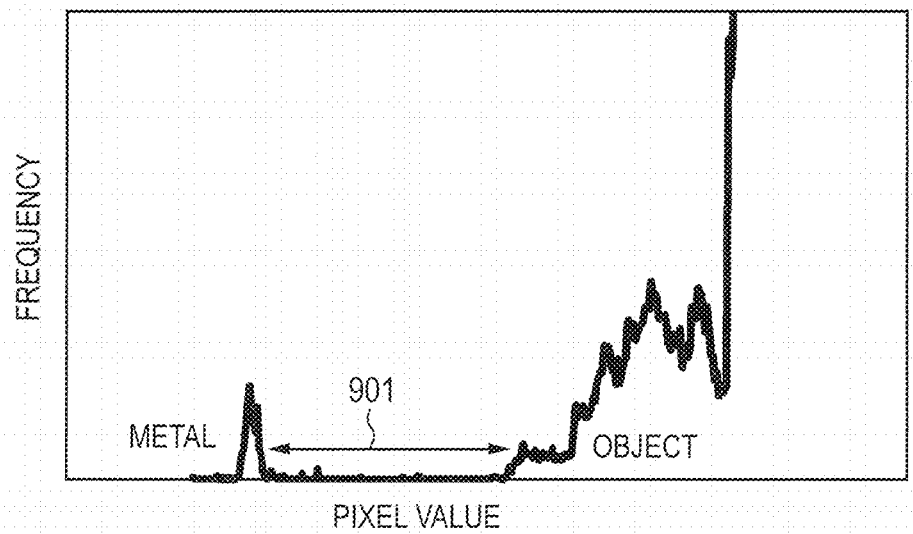
FIG. 11 is a diagram illustrating an example of an image histogram analysis in the fifth embodiment.

As another method, it is also possible to construct the apparatus in such a manner that the projection image is analysed, the metal and a portion other than the metal are automatically extracted, and the threshold value is set by using a difference between their values. For example, as illustrated in FIG. 11, if a histogram of the projection image is formed, since the metal portion strongly absorbs the X-ray, it has a peak in a low pixel value (i.e. a large number of low-valued pixels in the image will be represented as a peak in such a histogram). It is sufficient to detect such a peak and set a difference 901 between the peak and a distribution base of an object to be photographed to the threshold value ∈.

Figure 14:
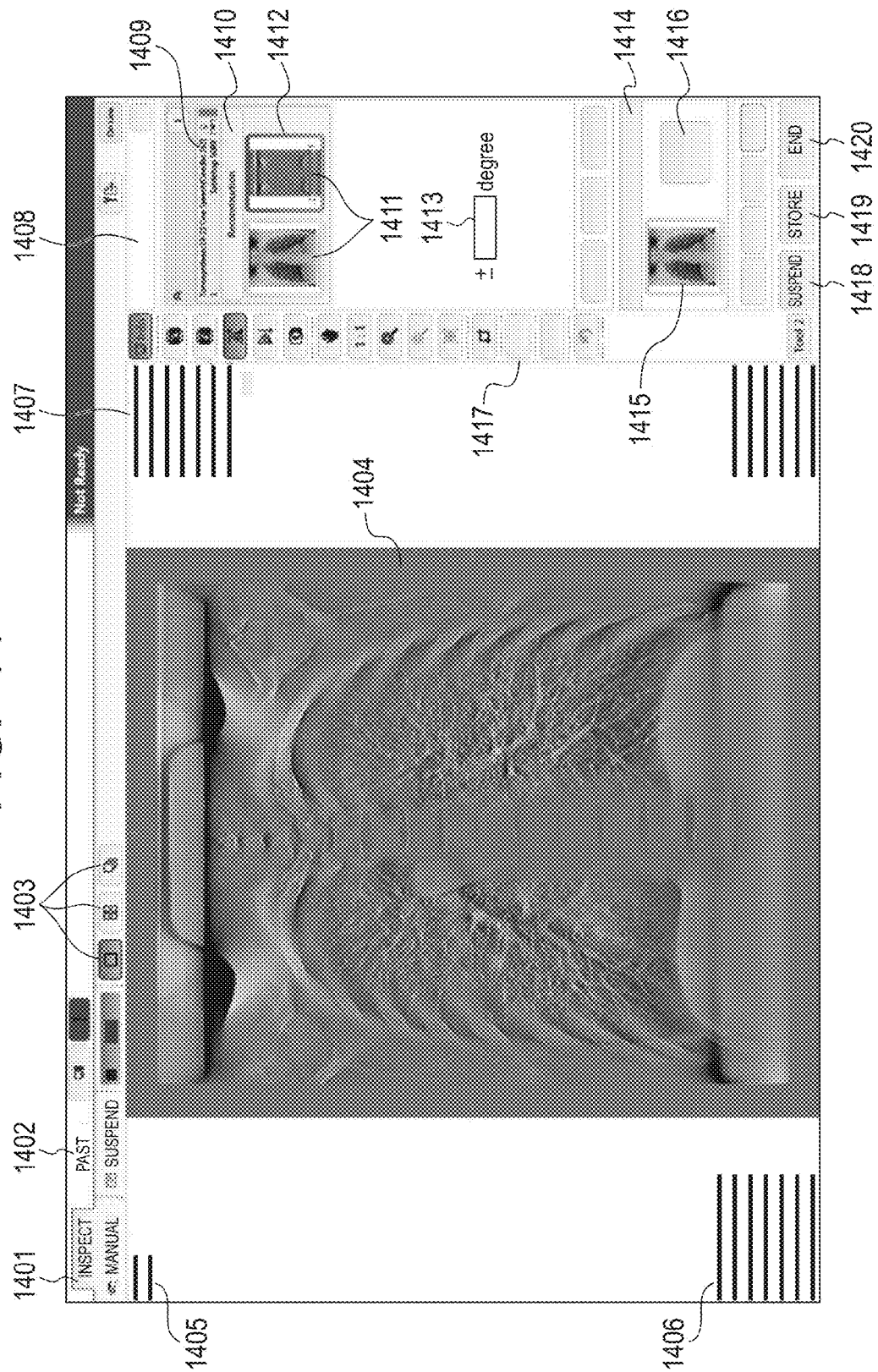
FIG. 14 is a diagram illustrating an example of the projection image in the first embodiment.

FIG. 14 is an example of a photographic display screen which is displayed on the monitor 110 by the display control unit of the X-ray photographic system control unit 108 according to the embodiment. The photographic display screen is a display screen which is used in such a manner that a cursor displayed likewise on the monitor 110 is operated by a mouse device or the like included in the operating unit 111, thereby photographing projection images and confirming the photographed images. Data of the photographed images on the display screen is stored in, for example, a memory in the X-ray photographic system control unit and is displayed in such a layout as shown in FIG. 14 in accordance with control of the display control unit.

An inspection information display tab 1401 is a display tab for displaying information regarding an inspection which is being progressed at present. The tab 1401 is displayed by the display control unit in accordance with information of the patient as a photographing target and the setting of a photographing mode. A past image display tab 1402 is a display tab for displaying information of the images which were photographed in the past. By clicking the display screen using the cursor position and the operating unit 111, the tab 1402 is displayed on the front face of the monitor 110 in place of the inspection information display tab. A display style change button 1403 is a button or a group of buttons for changing a display style of the radiography image which is displayed in a selection image display area 1404. In response to a click of the button by the mouse cursor, one of the following display styles is selected: a first display style in which only one selected image is displayed; a second display style in which a plurality of radiography images regarding the same inspection or same patient are arranged and displayed; and a third display style in which a plurality of projection images or frame images obtained by the tomosynthesis photography, radioscopy or cinemascope photography, or the like are arranged and displayed. The photographed images are displayed in the display style selected by the display control unit.

In the photographic display screen shown in FIG. 14, a selected tomographic image is displayed in the image display area 1404.

Patient information of the present inspection is displayed in a display area 1405. The patient information is, for example, information peculiar to the patient such as ID, name, sex, age, and the like of the patient. Execution information as information which was sent from the X-ray generating apparatus control unit 107 and is related with the radiation irradiation performed in association with the image which is being displayed is displayed in a display area 1406. The execution information is, for example, information regarding photographing time, total irradiation time, total area dose, total absorption dose, and total air kerma of a group of projection images which are used in the reconstruction of the tomographic image displayed in the image display area 1404. In addition to them, an amount of available memory of the HDD (hard disc drive) may be displayed as illustrated in FIG. 14. The photographic information set on the photographic apparatus side is displayed in a display area 1407. The photographic information is, for example, information regarding a tube voltage, an irradiation time, a tube current, an mAs value, a binning state, a frame rate, and the like. In addition to these, in the case where the image which is being displayed at present is a tomosynthesis image or a radioscopic or cinemascopic image, a frame number may be displayed.

Photograph reservation information and photograph-completion information regarding the patient who is being inspected at present are displayed in an inspection panel 1408. A photographing mode is displayed in a display area 1409. In the example of FIG. 14, photographing mode information is illustrated in a 2×2 table showing that the photography being performed is tomosynthesis photography with the object being photographed by a moving image sensor. A button 1410 is a button for displaying a setting display screen to make a setting for forming a reconstruction image from the group of projection images. A photographed thumbnail image is displayed in a display area 1411. In the example of FIG. 14, the following two thumbnail images are displayed: one is a representative image of a set of collected projection images and the other is a thumbnail of the formed reconstruction image. A selection display frame 1412 is a display area for displaying a selection state of the image to be displayed in the image display area 1404. By clicking the thumbnail image using the cursor, the clicked thumbnail image is selected by the display control unit and the selection display frame 1412 is displayed to a position surrounding the selected thumbnail image.

An irradiation angle setting GUI 1413 is a GUI (Graphical User Interface) for setting a magnitude of oscillation angle of the irradiating position of the X-ray tube 101 to the mechanism control unit 105 and the X-ray generating apparatus control unit 107 when the projection images are photographed. In one embodiment, the irradiation angle setting GUI is constructed in such a manner that in order to perform the setting efficiently in the case of setting the front and rear oscillation angles for the centre position of the FPD (flat panel radiation detector) so that they are equalized, if one numerical value is input, the setting of the oscillation angle is completed. For example, if 30 is input into the irradiation angle setting GUI 1413, the radiation is irradiated at the oscillation angle of ±30° (60° in total). The oscillation angle can be set to, for example, an acute angle between a line connecting the centre position of the X-ray detector 106 and the focal point of the X-ray tube 101 and a straight line which passes through the centre position of the X-ray detector 106 and is directed to the gravity direction. In this instance, for example, the X-ray photography system control unit 108 preliminarily holds the maximum value of the oscillation angles in a memory in accordance with identification information of the mechanism control unit 105 and the X-ray generating apparatus control unit 107 which are connected, so that when the oscillation angle which is equal to or larger than the maximum value is input, the display control unit can display a warning or a process for replacing the input value by the maximum value can be executed. The X-ray photography system control unit 108 can automatically transmit the information of the oscillation angle to the mechanism control unit 105 and the X-ray generating apparatus control unit 107 in accordance with the input to the irradiation angle setting GUI 1413.

In addition, a past image display panel 1414 is a display area for enabling the past images to be referred to on the inspection display screen 1401 without displaying the past image display tab 1402 to the front face. Thumbnails of the past images are displayed in a display area 1415. In the example of FIG. 14, the projection images of the tomosynthesis photography which were photographed in the past are displayed. A button 1416 is a button for allowing a display screen for selecting the past images displayed in the display area 1415 from a past image list to be displayed by the display control unit. An image adjustment panel 1417 is a display area in which a plurality of buttons for adjusting the images displayed in the selection image display area 1404 are arranged. For example, buttons for instructing the following operations are displayed: a rotation of ±90° of the image; a reversal in the upper/lower and right/left directions; a black and white reversal; a change in centre position of the display image to the image display area 1404; an equal magnification (life size) display; an enlargement or reduction; and an area selection. In addition to these, a button for resetting the adjustment which is made on the image adjustment panel 1417 or a check button for labelling a mark indicative of suitability to the image as a diagnosis image may be displayed. A button 1418 is an inspection reservation button for reserving the inspection which is being executed at present and selecting another inspection. A button 1419 is a button for outputting the current inspection image into storage. A button 1420 is a button for finishing the current inspection and terminating the display of the photographing display screen.

Figure 15A:
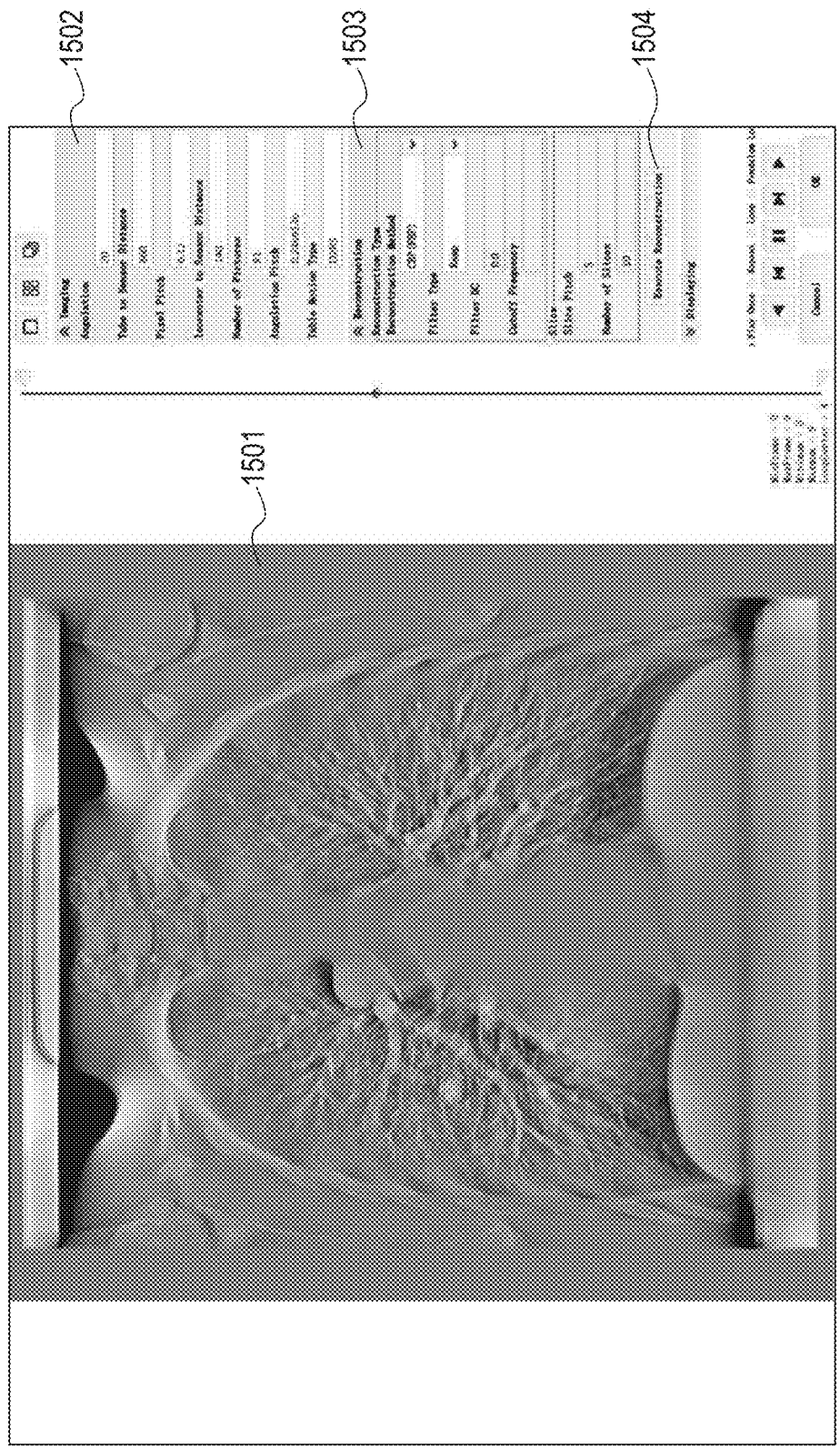
FIG. 15A is a diagram illustrating an example of a setting display screen of tomosynthesis in the first embodiment.
Figure 15B:
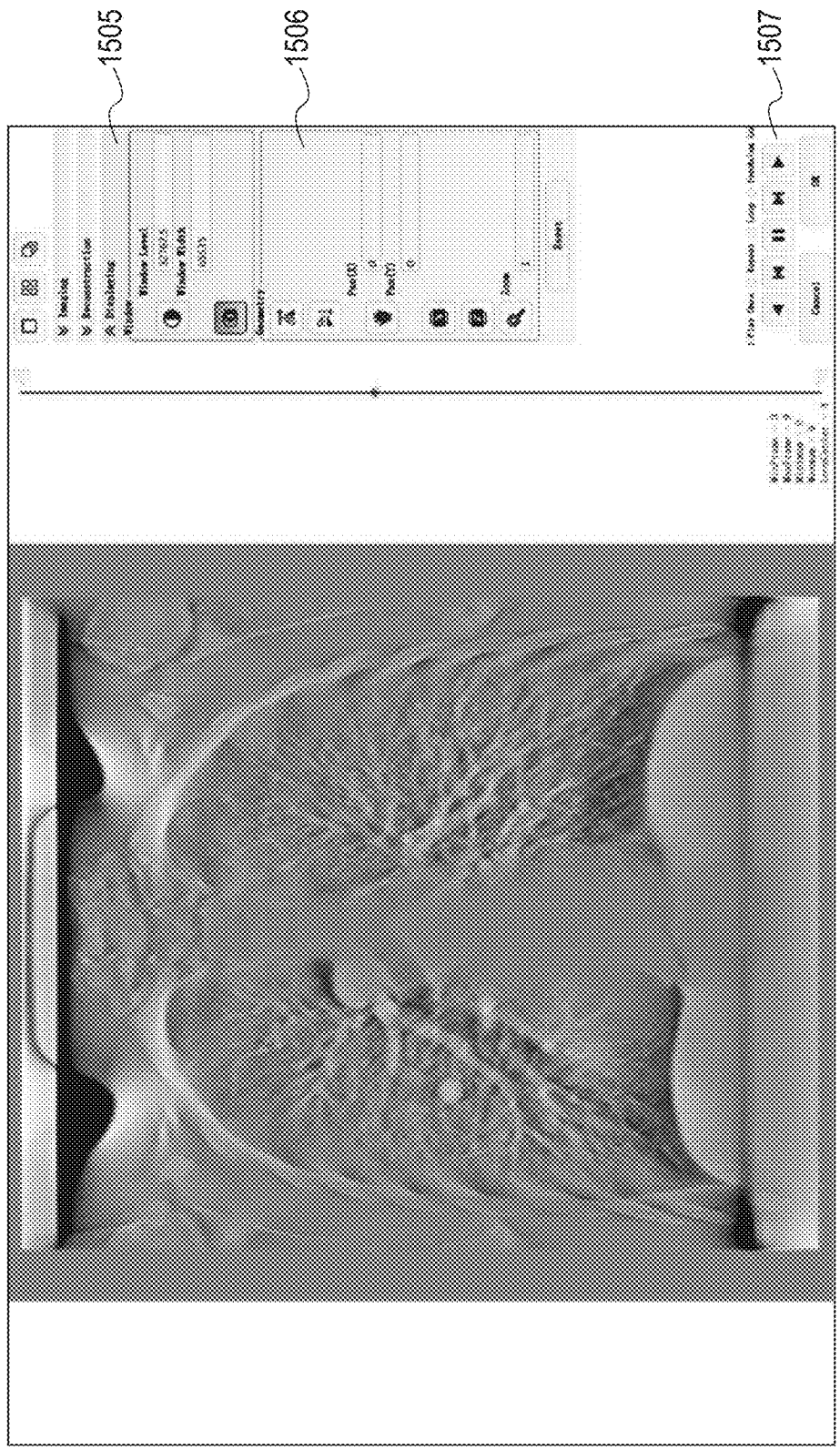
FIG. 15B is a diagram illustrating another example of the setting display screen of tomosynthesis in the first embodiment.

FIGS. 15A and 15B are diagrams each showing an example of a setting display screen of the tomosynthesis which is displayed to the display unit in response to the button 1410 being clicked at the cursor position. The reconstruction image which is obtained by the reconstructing process is displayed in an image display area 1501. An area 1502 is an area for displaying the execution information which is sent as execution results of the tomosynthesis photography from the photographing control unit 104, mechanism control unit 105, and X-ray generating apparatus control unit 107. For example, the following information is displayed: an oscillation angle; a distance between the X-ray tube 101 and the X-ray detector 106; a pixel pitch of the X-ray detector 106; a distance between the isocenter and the X-ray detector 106; the number of photographed projection images; a pitch of the oscillation angle; and identification information of a table. Although the information such as an oscillation angle or the like is information which has been preset on the photographic display screen illustrated in FIG. 14, the information of the oscillation angle is also transmitted as execution information from the mechanism control unit 105 and the X-ray generating apparatus control unit 107. This is because since it is strictly impossible to photograph at the oscillation angle which perfectly coincides with the set value due to an error, such information of the oscillation angle is used for the reconstructing process also in consideration of the difference after that. For example, the oscillation angle is set from the photographic apparatus in such a manner that the front and rear oscillation angles are equalized with respect to the moving direction of the X-ray tube 101 and the X-ray detector 106. However, strictly, it means that an error can occur on the order of below $10^{-1}$ degree of the oscillation angles.

In addition, a display area 1503 is a display area for setting reconstruction parameters. For example, the following items can be set: a reconstructing method such as filtered back projection, successive reconstruction, or the like; a reconstruction filter such as Ramp, Shepp & Logan, or the like; a DC component of the filter; a cut-off frequency; a pitch of reconstruction slices; the number of reconstruction slices; and the like.

A button 1504 is a button for instructing a disclosure of the reconstructing process on the basis of the setting. In accordance with such an operation that the button 1504 is clicked at the cursor position, the reconstructing process by the image processing unit 109 is started. After completion of the reconstructing process, the reconstruction image is displayed in the image display area 1502.

A display area 1505 in FIG. 15B is a GUI for setting a window level and a window width of the reconstruction image or the projection image. In this instance, the window level indicates, for example, a representative pixel value of the image and is, for example, a centre value of the image. The window width indicates a gradation width and is, for example, a value of a difference between an upper order 5% point and a lower order 5% point of the image. A display area 1506 is a setting area of geometrical information and a GUI for setting the following items is displayed in this area: a reversal in the right/left and upper/lower directions; a change in centre position of the displayed reconstruction image to the display area 1501; a rotation of ±90°; a zoom instruction; and a zoom ratio.

Each of the display areas 1502, 1503, 1505, and 1506 is expanded or contracted by the display control unit in accordance with the click at the cursor position. FIG. 15A illustrates a state where the display areas 1502 and 1503 are enlarged and the display areas 1505 and 1506 are contracted. FIG. 15B illustrates a state where the display areas 1505 and 1506 are enlarged and the display areas 1502 and 1503 are contracted.

Playback buttons 1507 are buttons for continuously switching the reconstruction images in order from the top or bottom and displaying and a group of buttons for instructing a reverse fast playback, a lower edge display, a play and pause, an upper edge display, and a forward fast display, respectively.

The examples of the representative embodiments of the invention have been described above. However, the invention is not limited to the foregoing embodiments illustrated in the drawings but can be properly modified and embodied within a range without changing its essence. For example, the invention can be also embodied in a form of a system, an apparatus, a method, a program, a storage medium, or the like. Specifically speaking, the invention may be applied to a system constructed by a plurality of apparatuses or to an apparatus constructed by a single piece of equipment.

<Other Embodiments>

The invention is also realized by executing the following processes. That is, software (program) for realizing the functions of the embodiments mentioned above is supplied to a system or apparatus through a network or various kinds of storage media and a computer (or a CPU, MPU (microprocessing unit, or the like) of the system or apparatus reads out the program and executes processes corresponding thereto.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2011-275380, filed Dec. 16, 2011, and 2012-225258, filed Oct. 10, 2012 which are hereby incorporated by reference herein in their entirety.

What is claimed is:

1. An image processing apparatus comprising:
   an obtaining unit configured to obtain a plurality of radiation projection images from a digital radiation detector;
   a reconstructing unit configured to execute a filtering process on the plurality of radiation projection images using a reconstruction filter and a reconstructing process to create a tomographic image on the basis of the obtained plurality of radiation projection images; and
   a processing unit, including a central processing unit, configured to reduce an influence on a value of a first pixel in a radiation projection image to be supplied to the reconstruction unit, the influence being exerted by a second pixel, in a case in which a difference between the value of the first pixel and the value of the second pixel is larger than a predetermined threshold value,
   wherein when an absolute value of the difference between the first pixel value and the second pixel value is smaller than the threshold value, the processing unit is configured to output the difference value, and when the absolute value of the difference is larger than the threshold value, the processing unit is configured to output a value smaller than the difference value; and
   wherein the reconstructing unit is configured to execute the reconstructing process of the tomographic image on the basis of a value output by the processing unit.

2. The image processing apparatus according to claim 1, wherein the first pixel is to be a target pixel of the filtering process in the reconstruction unit and the second pixel is a pixel peripheral to the first pixel and is to be used by the reconstruction unit in the filtering of the target pixel.

3. The image processing apparatus according to claim 1, wherein on the basis of a magnitude relation between the threshold value and the difference between the first pixel value and the second pixel value, the processing unit is configured to switch between outputting the difference value and outputting a value smaller than the difference value to the reconstructing unit.

4. The image processing apparatus according to claim 1, wherein the reconstructing unit is configured to convolution-process the output value with a reconstruction filter coefficient.

5. The image processing apparatus according to claim 4, wherein, when the output value and the reconstruction filter coefficient are convolution-processed, the reconstructing unit is configured to correct at least one of the output value and the reconstruction filter coefficient on the basis of a geometrical layout of the first pixel and a focal point of a radiation generating apparatus.

6. The image processing apparatus according to claim 1, wherein the reconstructing unit comprises a multiplying unit and a convolution unit configured to process each pixel output by the processing unit by filtering each pixel using the reconstruction filter coefficient, to output filtered values; and a back projection unit configured to add the output filtered values together to create a tomographic image.

7. The image processing apparatus according to claim 6, wherein the convolution unit is further configured to multiply the output filtered values by a coefficient based on a geometrical layout of: a reconstructing position, a focal point of a radiation generating apparatus, and a position of the pixel after the reconstruction filtering process; and
   wherein the back projection unit is configured to add the pixel values output by the convolution unit; and to obtain pixel values at each reconstructing position, thereby obtaining the tomographic image.

8. The image processing apparatus according to claim 1, further comprising a setting unit configured to set the threshold value on the basis of a difference between pixel values of two pixel positions designated by a user in one of the radiation projection images.

9. The image processing apparatus according to claim 1, further comprising a setting unit configured to set the threshold value on the basis of a difference between pixel values of two pixel positions which are automatically obtained by analysis of one of the radiation projection image.

10. An image processing apparatus for reconstructing a tomographic image from a plurality of projection images obtained by irradiating a subject with radiation from a plurality of directions, the apparatus comprising:
    an obtaining unit configured to obtain, for each of the plurality of projection images, a weighting coefficient according to a difference between a pixel value of a filtering target pixel and a pixel value of a second pixel;
    a reconstructing unit configured to process each pixel of the plurality of projection images on the basis of a reconstruction filter coefficient weighted by the weight coefficient and to reconstruct the tomographic image based on the processed pixels;
    a calculating unit configured to calculate a difference value between a filtering target pixel of a projection image and a peripheral pixel of the target pixel;
    an output unit configured to output the weighting coefficient which is smaller as an absolute value of the calculated difference value is larger;
    a multiplying unit configured to multiply a filter coefficient by the weighting output by the output unit; and
    a processing unit, including a central processing unit, configured to filter a plurality of projection images on the basis of a result obtained by the multiplying unit.

11. The image processing apparatus according to claim 10, wherein the obtaining unit is configured to obtain the weighting coefficient which is smaller as a distance between the filtering target pixel and the second pixel is larger.

12. The image processing apparatus according to claim 10, wherein the calculating unit is configured to calculate a sign of the difference value; and
    wherein the output unit is configured to output a predetermined weighting coefficient if the difference value has a first sign, and to output a weighting coefficient which is smaller as the absolute value of the difference value is larger when the difference value has an opposite sign.

13. The image processing apparatus according to claim 10, further comprising a setting unit configured to set the weighting coefficient on the basis of the difference between pixel values of two pixel positions designated by a user in the projection image.

14. The image processing apparatus according to claim 10, further comprising a setting unit configured to set the weighting coefficient on the basis of the difference between pixel values of two pixel position which are automatically obtained by analysis of the projection image.

15. An image processing method of reconstructing a tomographic image from a plurality of projection images, the method comprising:
    an obtaining step to obtain a plurality of radiation projection images from a digital radiation detector;
    a reconstructing step to execute a filtering process on the plurality of radiation projection images using a reconstruction filter and a reconstructing process to create a tomographic image on the basis of the obtained plurality of radiation projection images; and
    a processing step to reduce an influence on a value of a first pixel in a radiation projection image to be supplied to the reconstruction unit, the influence being exerted by a second pixel, in a case in which a difference between the value of the first pixel and the value of the second pixel is larger than a predetermined threshold value,
    wherein when an absolute value of the difference between the first pixel value and the second pixel value is smaller than the threshold value, the processing step outputs the difference value, and when the absolute value of the difference is larger than the threshold value, the processing step outputs a value smaller than the difference value; and
    wherein the reconstructing step executes the reconstructing process of the tomographic image on a basis of a value output by the processing step.

16. An image processing method of reconstructing a tomographic image from a plurality of projection images obtained by irradiating a subject with radiation from a plurality of directions, the method comprising:
    an obtaining step to obtain, for each of the plurality of projection images, a weighting coefficient according to a difference between a pixel value of a filtering target pixel and a pixel value of a second pixel;
    a reconstructing step to process each pixel of the plurality of projection images on the basis of a reconstruction filter coefficient weighted by the weight coefficient and to reconstruct the tomographic image based on the processed pixels;
    a calculating step to calculate a difference value between a filtering target pixel of a projection image and a peripheral pixel of the target pixel;
    an outputting step to output the weighting coefficient which is smaller as an absolute value of the calculated difference value is larger;
    a multiplying step to multiply a filter coefficient by the weighting output by the outputting step; and
    a processing step to filter a plurality of projection images on the basis of a result obtained by the multiplying step.

17. A non-transitory computer-readable storage medium storing a computer program for causing a computer to execute the image processing method according to claim 15.

18. A non-transitory computer-readable storage medium storing a computer program for causing a computer to execute the image processing method according to claim 16.

19. An image processing apparatus comprising:
    an obtaining unit configured to obtain a plurality of radiation projection images from a digital radiation detector;
    a reconstructing unit configured to execute a filtering process on the plurality of radiation projection images using a reconstruction filter and a reconstructing process to create a tomographic image on the basis of the obtained plurality of radiation projection images; and
    a processing unit, including a central processing unit, configured to reduce an influence on a value of a first pixel in a radiation projection image to be supplied to the reconstruction unit, the influence being exerted by a second pixel, in a case in which a difference between the value of the first pixel and the value of the second pixel is larger than a predetermined threshold value,
    wherein, on the basis of a magnitude relation between the threshold value and the difference between the first pixel value and the second pixel value, the processing unit is configured to switch between outputting the difference value and outputting a value smaller than the difference value to the reconstruction unit, and
    wherein the reconstructing unit is configured to execute the reconstruction process of the tomographic image on the basis of the value output by the processing unit.

20. An image processing apparatus comprising:
    an obtaining unit configured to obtain projection images of an object from a digital radiation detector; and
    a processing unit, including a central processing unit, configured to, for each of pixels of each of the obtained projection images, as a target pixel, perform a reconstruction filtering process in order to obtain a plurality of filtered data, based on the target pixel and a pixel different from the target pixel, the different pixel being in one of the projection images including the target pixel, and generate a tomographic image based on the obtained plurality of filtered data,
    wherein the processing unit processes the target pixel with a reconstruction filtering coefficient based on a value of the target pixel and a value of the different pixel, and with a correction coefficient based on a difference value between the value of the target pixel and the value of the different pixel, and
    wherein the processing unit determines an absolute value of the correction coefficient as a value smaller than an absolute value of the difference value in a case where the absolute value of the difference value is larger than a threshold value.

21. The image processing apparatus of claim 20, wherein the processing unit further determines the correction coefficient as the difference value in a case where the absolute value of the difference value is smaller than the threshold value.

22. The image processing apparatus according to claim 20, wherein the reconstruction filtering process convolution-processes an output value with the reconstruction filter coefficient.

23. The image processing apparatus according to claim 22, wherein, when the output value and the reconstruction filter coefficient are convolution-processed, the reconstruction filtering process corrects at least one of the output value and the reconstruction filter coefficient on the basis of a geometrical layout of a first pixel and a focal point of a radiation generating apparatus.

24. The image processing apparatus according to claim 20, wherein the reconstruction filtering process employs a multiplying unit and a convolution unit configured to process each pixel output by the processing unit by filtering each pixel using the reconstruction filter coefficient, to output filtered values; and a back projection unit configured to add the output filtered values together to create a tomographic image.

25. The image processing apparatus according to claim 24, wherein the convolution unit is further configured to multiply the output filtered values by a coefficient based on a geometrical layout of: a reconstructing position, a focal point of a radiation generating apparatus, and a position of the pixel after the reconstruction filtering process; and
    wherein the back projection unit is configured to add the pixel values output by the convolution unit; and to obtain pixel values at each reconstructing position, thereby obtaining the tomographic image.

26. The image processing apparatus according to claim 20, further comprising a setting unit configured to set the threshold value on the basis of a difference between pixel values of two pixel positions designated by a user in one of the radiation projection images.

27. The image processing apparatus according to claim 20, further comprising a setting unit configured to set the threshold value on the basis of a difference between pixel values of two pixel positions which are automatically obtained by analysis of one of the radiation projection images.

28. An image processing method of reconstructing a tomographic image from a plurality of projection images, the method comprising:
- an obtaining step to obtain projection images of an object from a digital radiation detector; and
- a processing step to, for each of pixels of each of the obtained projection images, as a target pixel, perform a reconstruction filtering process in order to obtain a plurality of filtered data, based on the target pixel and a pixel different from the target pixel, the different pixel being in one of the projection images including the target pixel, and generate a tomographic image based on the obtained plurality of filtered data,
- wherein the processing step processes the target pixel with a reconstruction filtering coefficient based on a value of the target pixel and a value of the different pixel, and with a correction coefficient based on a difference value between the value of the target pixel and the value of the different pixel, and
- wherein the processing step determines an absolute value of the correction coefficient as a value smaller than an absolute value of the difference value in a case where the absolute value of the difference value is larger than a threshold value.

29. A non-transitory computer-readable storage medium storing a computer program that causes a computer to execute the image processing method according to claim 28.

30. An image processing apparatus comprising:
- at least one central processing unit; and
- a memory storing a program including instructions to be executed by the at least one processor to perform a method comprising:
- obtaining projection images of an object from a digital radiation detector;
- performing, for each of pixels of each of the obtained projection images, as a target pixel, a reconstruction filtering process in order to obtain a plurality of filtered data, based on the target pixel and a pixel different from the target pixel, the different pixel being in one of the projection images including the target pixel; and
- generating a tomographic image based on the obtained plurality of filtered data,
- wherein in the performing, (a) the target pixel is processed with a reconstruction filtering coefficient based on a value of the target pixel and a value of the different pixel, and with a correction coefficient based on a difference value between the value of the target pixel and the value of the different pixel and (b) an absolute value of the correction coefficient is a value smaller than an absolute value of the difference value in a case where the absolute value of the difference value is larger than a threshold value.

* * * * *